(12) United States Patent
Moe

(10) Patent No.: US 6,666,885 B2
(45) Date of Patent: Dec. 23, 2003

(54) HEART VALVE LEAFLET

(75) Inventor: Riyad Moe, Austin, TX (US)

(73) Assignee: Carbomedics Inc., Austin, TX (US)

( * ) Notice: Subject to any disclaimer, the term of this patent is extended or adjusted under 35 U.S.C. 154(b) by 103 days.

(21) Appl. No.: 09/940,361

(22) Filed: Aug. 27, 2001

(65) Prior Publication Data

US 2002/0045936 A1 Apr. 18, 2002

Related U.S. Application Data

(63) Continuation-in-part of application No. 09/292,914, filed on Apr. 16, 1999, now Pat. No. 6,283,994.

(51) Int. Cl.[7] ................................................. A61F 2/24
(52) U.S. Cl. ..................................................... 623/2.12
(58) Field of Search ................................ 623/2.1, 2.12, 623/2.13, 2.14, 2.15, 2.16, 2.17, 2.18, 2.19, 2.33

(56) References Cited

U.S. PATENT DOCUMENTS

| 4,222,126 A | 9/1980 | Boretos et al. ............. 623/2.19 |
| 4,364,127 A | 12/1982 | Pierce et al. ..................... 3/1.5 |
| 4,372,743 A | 2/1983 | Lane ........................... 623/2.12 |
| 4,759,759 A | 7/1988 | Walker et al. .............. 623/2.16 |
| 4,778,461 A | 10/1988 | Pietsch et al. .............. 623/2.13 |
| 5,376,113 A | 12/1994 | Jansen et al. .................... 623/2 |
| 5,500,016 A | 3/1996 | Fisher ............................. 623/2 |

FOREIGN PATENT DOCUMENTS

| DE | 196 24 948 A1 | 2/1998 |
| DE | 196 25 202 A1 | 2/1998 |
| FR | 2 788 217 A1 | 7/2000 |
| WO | 98/32400 | 7/1998 |

OTHER PUBLICATIONS

Knierbein, B., et al., Cad–Design, Stress Analysis and In Vitro Evaluation of Three Leaflet Blood–Pump Valves, J. Biomed. Eng. 1992, vol. 14, Jul., pp. 275–286.

Primary Examiner—David J. Isabella
(74) Attorney, Agent, or Firm—Williams, Morgan & Amerson, P.C.

(57) ABSTRACT

A heart valve is disclosed which includes a valve body and a plurality of flexible leaflets coupled to the valve body. The plurality of leaflets can have an open position and a closed position. Each of the plurality of leaflets can comprise a belly when the plurality of leaflets are in their respective closed positions. The belly of one or more of the plurality of leaflets preferably has a continuous curvature except for two or more features.

17 Claims, 8 Drawing Sheets

HEART VALVE LEAFLET

CROSS-REFERENCE TO RELATED APPLICATIONS

This application is a continuation-in-part of U.S. patent application Ser. No. 09/292,914, titled "Heart Valve Leaflet" and filed Apr. 16, 1999 now U.S. Pat. No. 6,283,994 by Moe, et al. and is incorporated herein by reference.

FIELD OF THE INVENTION

The present invention relates to valves and in particular to heart valve prostheses having a plurality of flexible leaflets.

BACKGROUND OF THE INVENTION

Ever since 1950, when blood oxygenators made open heart surgery feasible, it has been possible to treat some forms of heart disease by replacing one of the patient's heart valves with a prosthetic valve. Early heart valve prostheses included ball-and-cage valves and disc-and-cage valves in which a ball or a disc was housed in a cage. One side of the cage provided an orifice through which blood flowed either into or out of the heart, depending on the valve being replaced. When blood flowed in a forward direction, the energy of the blood flow forced the ball or disc to the back of the cage allowing blood to flow through the valve. When blood attempted to flow in a reverse direction, or regurgitate, the energy of the blood flow forced the ball or disc into the orifice in the valve and blocked the flow of blood.

A tri-leaflet valve includes an annular valve body in which three leaflets are mounted to a portion of the valve body, called a stent, located at the circumference of the annulus. The edge of each leaflet which is mounted to the valve body is called the attachment edge. Any edge of a leaflet which is not mounted to a valve body is called a "free margin." When blood flows in the forward direction, the energy of the blood flow deflects the three leaflets away from the center of the annulus and allows blood to flow therethrough. When blood flows in the reverse direction, the three leaflets engage each other in coaptive regions in which the free margins of the leaflets abut each other, occlude the valve body annulus and prevent the flow of blood. The valve leaflets are made from tissue, such as specially treated porcine or bovine pericardial tissue, or from man-made materials such as ceramic materials, elastomers or other biocompatible polymers.

One difficulty with valve prostheses is the amount of force required to open the leaflets to allow blood flow therethrough. Similarly, another issue is the amount of force required to close the leaflets. In conventional tri-leaflet valves, for example, the amount of force required to open the leaflets can be relatively high. This requirement is present in those valves made of polymeric material which include leaflets which present a convex or dome surface to the flow of blood in the forward direction when the leaflets are in a closed position. The amount of pressure needed to overcome the resistance to opening which is present due to the presentation of a dome to the blood flow is greater than other geometries. This excess pressure requirement can hinder the functioning of the valve and may prevent the valve from opening when necessary due to lack of sufficient force provided by the blood flow.

In addition, it is often important that the valve begin opening at a free margin of one or more of the leaflets. This enables blood flow to proceed as soon as a force of the blood flow acts on the leaflets because the free margins are open. If the initial blood flow acts on the lower portion of the leaflets and begins the opening sequence away from the free margin, then blood flow through the valve is delayed until the force finally displaces the free margins.

Therefore, there is a need to provide a heart valve prosthesis design to reduce the forward (systolic) pressure necessary to open the heart valve.

SUMMARY OF THE INVENTION

In general, in one aspect, the invention can include a heart valve comprising a valve body having a plurality of leaflets. The plurality of leaflets can be coupled to the valve body, and each of the plurality of leaflets is capable of having an open position and a closed position. One or more of the plurality of leaflets can have two or more features. The features can be formed as part of the leaflets.

In another aspect, the heart valve described above can have only two features.

In general, in one aspect, the invention can include a heart valve comprising a valve body having a plurality of leaflets. The plurality of leaflets can be coupled to the valve body, and each of the plurality of leaflets is capable of having an open position and a closed position. One or more of the plurality of leaflets can have two or more features, and the two or more features comprise one or more of the group consisting of planar regions, semicircular regions, folded regions, peaked regions, ridged regions, regions that are thicker than the rest of the leaflet, regions that are thinner than the rest of the leaflet and sine-wave shaped regions.

In general, in another aspect, the invention can include a heart valve comprising a valve body having a plurality of leaflets. The plurality of leaflets can be coupled to the valve body, and each of the plurality of leaflets is capable of having an open position and a closed position. One or more of the plurality of leaflets can have two or more features. Each of the plurality of the leaflets can have a line that extends from the bottom point of the leaflet to the center of the free margin. In one aspect, the two or more features are symmetrically disposed around this line of the one or more of the plurality of leaflets. In another aspect, the two or more features are asymmetrically disposed around this line of the one or more of the plurality of leaflets.

In general, in another aspect, the invention can include a heart valve comprising a valve body. A plurality of leaflets can be coupled to the valve body. Each of the plurality of leaflets can have an open position and a closed position. Each of the plurality of leaflets can have a line that extends from the bottom point of the leaflet to the center of the free margin. One or more of the plurality of leaflets comprises two or more features. The features comprise an axis. The inclination of the axis of the features with respect to the line should be less than 10 degrees.

In general, in another aspect, the invention can include a heart valve comprising a valve body and a plurality of flexible leaflets coupled to the valve body. The plurality of leaflets should have an open position and a closed position. Each of the plurality of leaflets can comprise a belly when the plurality of leaflets are in their respective closed positions. The belly of one or more of the plurality of leaflets preferably has a continuous curvature except for a non-continuous portion. Alternatively, each leaflet can comprise a belly having a predominately first curvature in the open position and a predominately second curvature in the closed position.

In general, in another aspect, the invention can include a heart valve comprising a valve body and a plurality of flexible leaflets coupled to the valve body. Each leaflet has a thickness. One or more of the plurality of leaflets can comprise a buckle-susceptible portion, the thickness of the buckle-susceptible portion being different from the thickness of the remaining portion of the leaflet.

In general, in another aspect, the invention can include a heart valve comprising a valve body and a plurality of flexible leaflets coupled to the valve body. The plurality of leaflets should have an open position and a closed position. One or more of the plurality of leaflets can comprise an expansion feature such a folded, peaked or ridged region. The expansion feature is preferably configured so that the leaflet has more surface area in the open position than it has in the closed position.

DESCRIPTION OF PREFERRED EMBODIMENTS

Figure 1:
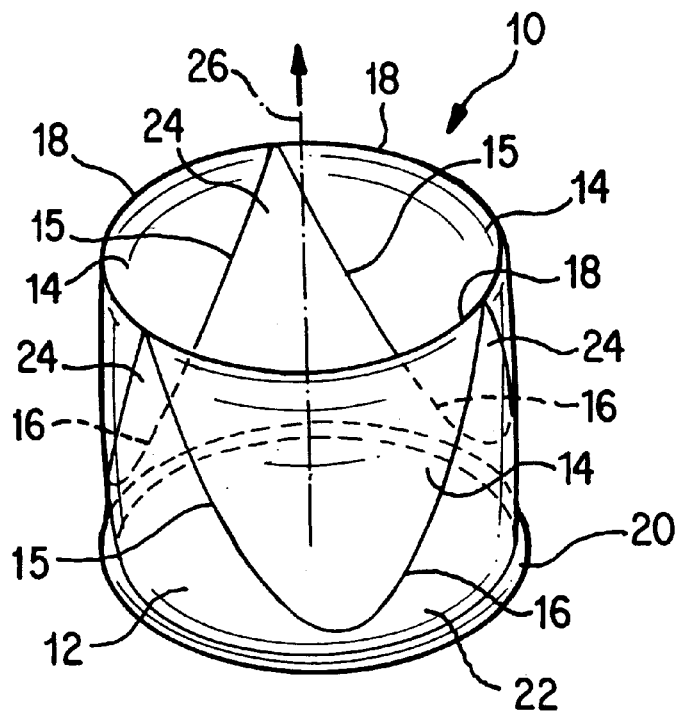
FIG. 1 is a perspective view of a polymer valve.

As will be recognized, based on the present disclosure, many different embodiments or versions of the invention, defined by the appended claims, can be made. A description of various preferred embodiments is set forth below. One non-limiting example is shown in FIG. 1. A tri-leaflet heart valve prosthesis 10 comprises an annular elastic valve body 12 and three flexible leaflets 14 made of a biocompatible polymer such as silicone or polyurethane, as shown in FIG. 1. Each leaflet has an attachment edge 15 by which the leaflet is coupled to the valve body along an attachment curve 16. Each leaflet has a free edge 18 (also referred to as a "free margin") which is the edge of the leaflet that is not mounted to the valve body. A sewing ring 20 or other attachment member is coupled to the base of the valve body 12 to provide a place for sutures to be applied when the valve is implanted in a patient. The valve body comprises an annular base 22 and a leaflet support, comprising three shaped posts 24, that support the leaflets 14.

Figure 2:
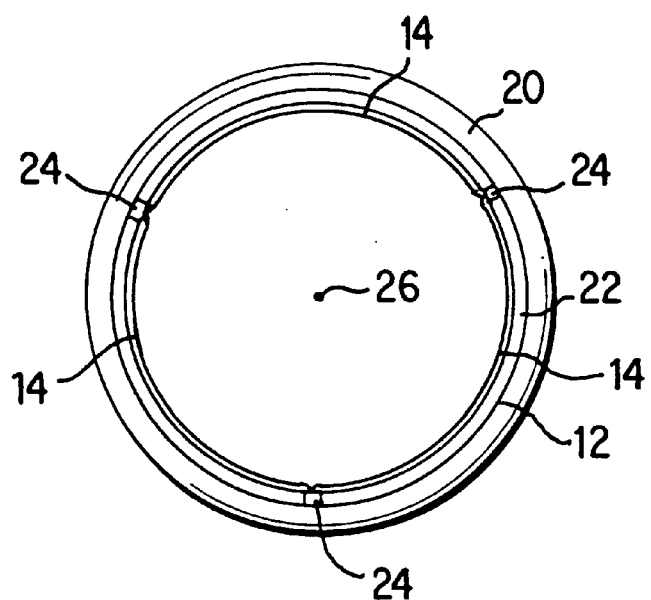
FIG. 2 is a top view of the polymer valve of FIG. 1.

When fluid flow is in the forward direction, i.e., in the direction of the arrow shown in FIG. 1, the pressure of the blood flow causes the leaflets 14 to deflect away from a central longitudinal axis 26 of the valve body that is generally parallel to the three posts 24. In this "open" position, the leaflets 14 define a large flow orifice, as shown in FIG. 2 and the valve presents little resistance to fluid flow.

Figure 3:
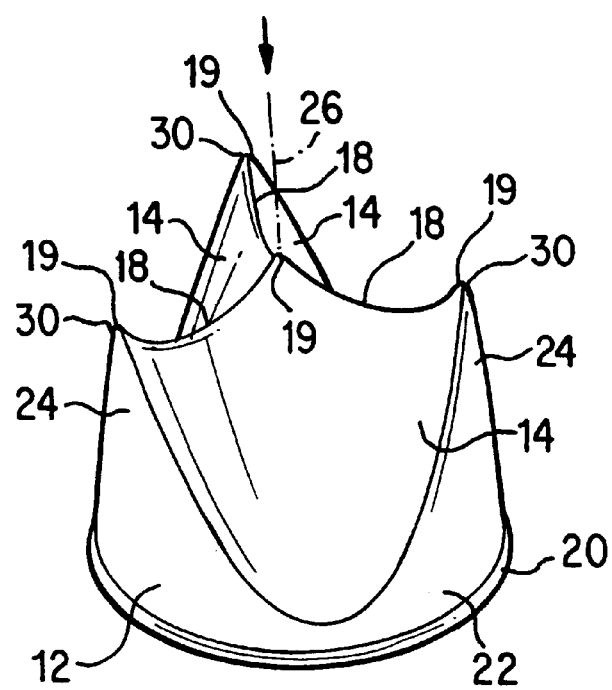
FIG. 3 is a perspective view of a polymer valve.
Figure 4:
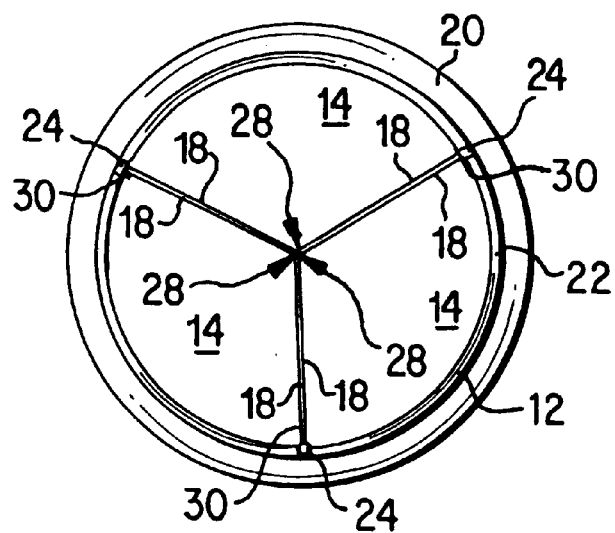
FIG. 4 is a top view of the polymer valve of FIG. 3.

When the pressure of blood flow is insufficient to overcome the elastic force biasing the valve toward a closed or partially closed position, the leaflets deflect toward axis 26, as shown in FIGS. 3 and 4. In this "closed" position, each leaflet may occlude more than one-third of the valve body's orifice were it not for the presence of the other leaflets. Consequently, when the three leaflets deflect toward axis 26, they engage each other and form coaptive areas along the free edges 18 which help the valve seal against reverse flow. Coaptive areas are shown in FIG. 3, generally as regions where leaflets abut one another. Further, when the leaflets press together, each leaflet contributes to the formation of a "triple point" 28 at the point where the three leaflets come together, as shown in FIG. 4. The triple point 28 is formed by the intersection of the centers of the free margins 18 of the leaflets. The place where the leaflets 14 come together adjacent the posts 24 is called the "commissure" 30, as shown in FIG. 3.

In most prior art heart valves, the flexible leaflets in their closed positions are generally planar in their coaptive regions and have a generally dome surface or shape in the region below the coaptive region, called the "belly". The pressure of blood flowing in a forward direction impinges on the convex side of the leaflets urging them from the closed positions shown in FIGS. 3 and 4 to the open positions shown in FIGS. 1 and 2. To make that transition, the blood pressure must overcome the resistance of the leaflets to buckling.

Figure 5A:
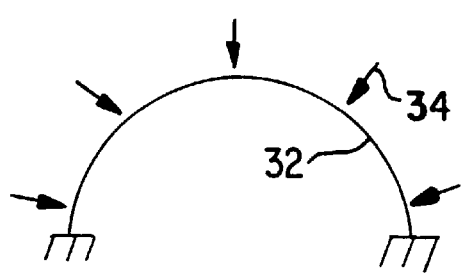
FIGS. 5a–d are cross-sectional views of a prior art leaflet being subjected to forward pressure.

This principal is illustrated in FIGS. 5a–d. A leaflet 32, the belly of which has a cylindrical cross-section as shown in FIG. 5a, has pressure 34, representing the pressure of blood attempting to flow in the forward direction (the direction of the arrow in FIG. 1) impinging on its convex side. The leaflet 32 resists displacement as a result, at least partially, of the dome shape of the leaflet. As the pressure 34 increases on the convex side, indicated by FIGS. 5b and 5c, the leaflet continues to resist displacement from its original position. Finally, when the pressure reaches a particular threshold level, the leaflet buckles and transitions from its closed position to its open position, illustrated in FIG. 5d.

It is believed that a change in curvature of the leaflet created by a planar feature, for example, disrupts the dome shape of the leaflet and enables opening forces, such as the force created by blood flow, to act on the flattened surface to open the leaflet under less pressure than is required when the leaflet forms a domed surface. In another embodiment, concave features are introduced into the otherwise-convex shape of leaflets. In still other embodiments, semicircular features or folded features are introduced into the leaflets. In still another embodiment, peaked or ridged features may be introduced into the shape of the leaflets.

A "feature" is introduced into the shape of the leaflet 32, which causes the leaflet to transition from its closed position to its open position at a lower forward pressure. As used herein, the term "feature" means any change in the leaflet that reduces its resistance to buckling, including a change in the curvature of the leaflet that causes the resulting leaflet to have a non-continuous shape or a reduction in the thickness of a portion of the leaflet. Such changes in the leaflet render parts of the leaflet less able to resist pressure, and thus provide an area in the leaflet which is the starting point of leaflet buckling in response to pressure. Such an area may thus be a type of "feature." Thus, a feature allows the beginning of leaflet opening at a lower pressure than that required to achieve the opening of a leaflet without a feature.

Figure 6A:
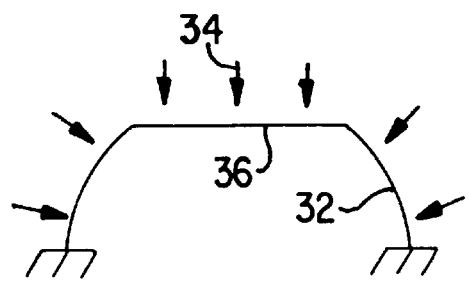
FIGS. 6a–d are cross-sectional views of a leaflet according to the present invention being subjected to forward pressure.
Figure 5B:
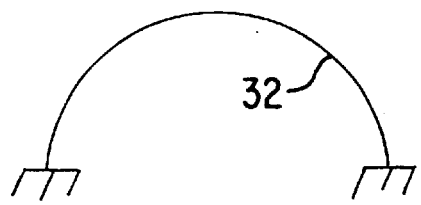
Figure 6B:
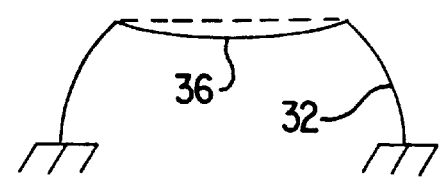
Figure 5C:
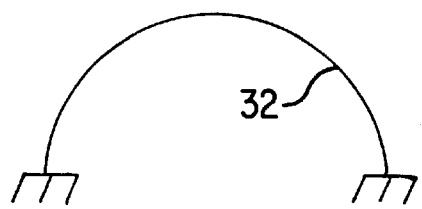
Figure 6C:
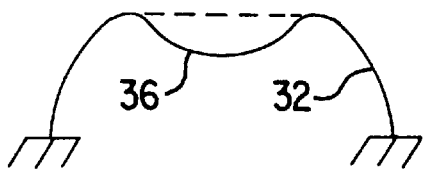
Figure 5D:
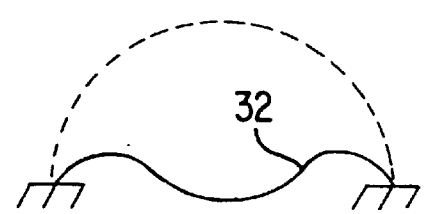
Figure 6D:
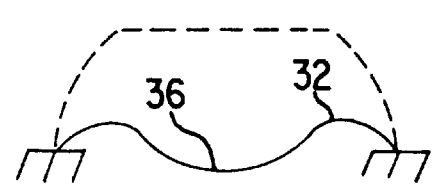

To illustrate a change in the curvature of the leaflet, a planar feature 36 can be introduced into the belly of the leaflet 32 so that the belly of the leaflet 32 no longer has a continuous dome shape, as shown in FIG. 6a. The planar feature 36 provides a lever area in the leaflet 32 which acts to open the leaflet 32 under pressure. As a consequence, the leaflet has a lower resistance to buckling as shown in FIGS. 6b–d. In FIG. 6b, in which the leaflet 32 is experiencing the same forward pressure as in FIG. 5b, the planar feature 36 has begun to deflect in the direction of the forward pressure. In FIG. 6c, in which the leaflet 32 is experiencing the same forward pressure as in FIG. 5c, the buckling of the planar feature 36 has begun to cause the remainder of the leaflet to deform. Under that same pressure, the leaflet will buckle entirely as shown in FIG. 6d and will make the transition from its closed position to its open position.

Figure 7:
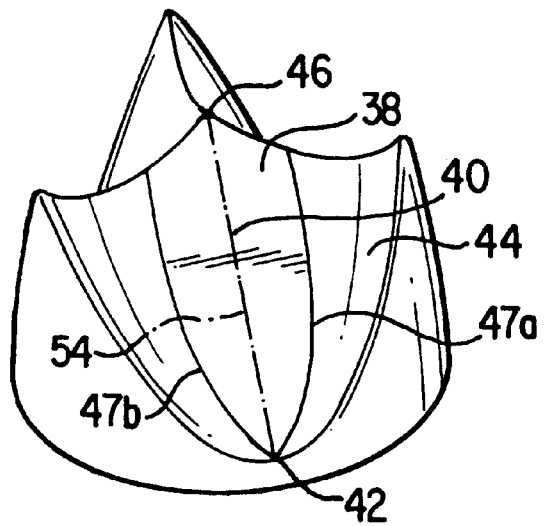
FIGS. 7 and 8 are perspective views of valves according to the present invention.

In one embodiment, illustrated in FIG. 7, a planar feature 38 extends from the bottom point 42 to the center of the free margin 46 and includes the area bounded by lines 47a, 47b. In another embodiment, the planar feature may be an area that extends to the center of the free margin but not to the bottom point. In still another embodiment, the planar feature may extend to the bottom point but not to the center of the free margin. In still another embodiment, the planar feature does not extend to either the center of the free margin or the bottom point.

An axis 54 of the planar portion may be parallel to, and coextensive with, a line 40, which extends from the bottom point 42 of the leaflet 44 to the center of free margin 46, or it may be inclined, preferably by less than ten degrees, with respect to the line 40.

Figure 8:
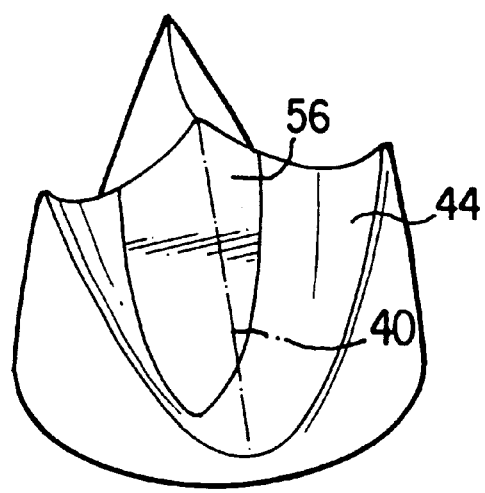

In the embodiment illustrated in FIG. 7, the planar feature 38 is symmetrical around the line 40 extending from the center of the free margin 46 of the leaflet 44 to the bottom point 42 of the leaflet 44. Such symmetrically located features are called "spines". The planar feature will reduce the leaflet's resistance to buckling even if it is not symmetrically located. Thus, the planar feature 56 may be asymmetrically located with respect to the line 40, as shown in FIG. 8. Alternatively, the planar feature may be obliquely located with respect to the line. In still another alternative, the planar feature may be transverse to the line. In each of these embodiments, the feature may extend to the free margin or attachment curve of the leaflet, or the boundaries of the feature may not intersect the boundaries of the leaflet.

The features may be located symmetrically or asymmetrically with respect to the line 40 of the leaflets and still achieve the result of reducing the resistance of the leaflets to buckling. Asymmetry can create unbalanced loads which provide an advantage in opening the valve.

Further, the features can have any arbitrary shape, including a sine-wave shape, as long as the continuity of the shape of the leaflets is interrupted by the feature or features.

Features may also be reductions in the thickness of portions of the leaflet. The thinness of the material in the features causes the features to buckle more easily than they would had the material in these areas been the same thickness as in the rest of the leaflet. Consequently, each leaflet buckles and transitions from a closed position to an open position more easily. The thin portions of the leaflet can be located anywhere along the leaflet's free margins or attachment edges.

The thickness of the material forming a feature may vary. For example, the feature may extend along a line from a leaflet's bottom point to the center of its free margin. The thickness of the material forming the feature may taper from its thickest point at the end of the feature closest to the center of the free margin to its thinnest point at the end of the feature closest to the bottom point. Alternatively, the material may be thickest at the end of the feature closest to the bottom point. The taper may be gradual and uniform or it may include a step increase or some other non-linear variation in thickness.

Some of the embodiments described above, particularly the embodiment having folded features, have the advantage of providing additional surface area for the leaflet. Consequently, when the leaflet is in the open position, leaflets open wider and the orifice illustrated in FIGS. 1 and 2 is larger, which decreases the valve's resistance to the flow of blood, a desirable characteristic in a heart valve. Further, in these embodiments, the membrane stresses in the leaflet are reduced because the leaflet does not need to be forced into a fully open position to form the orifice illustrated in FIGS. 1 and 2.

Figure 10:
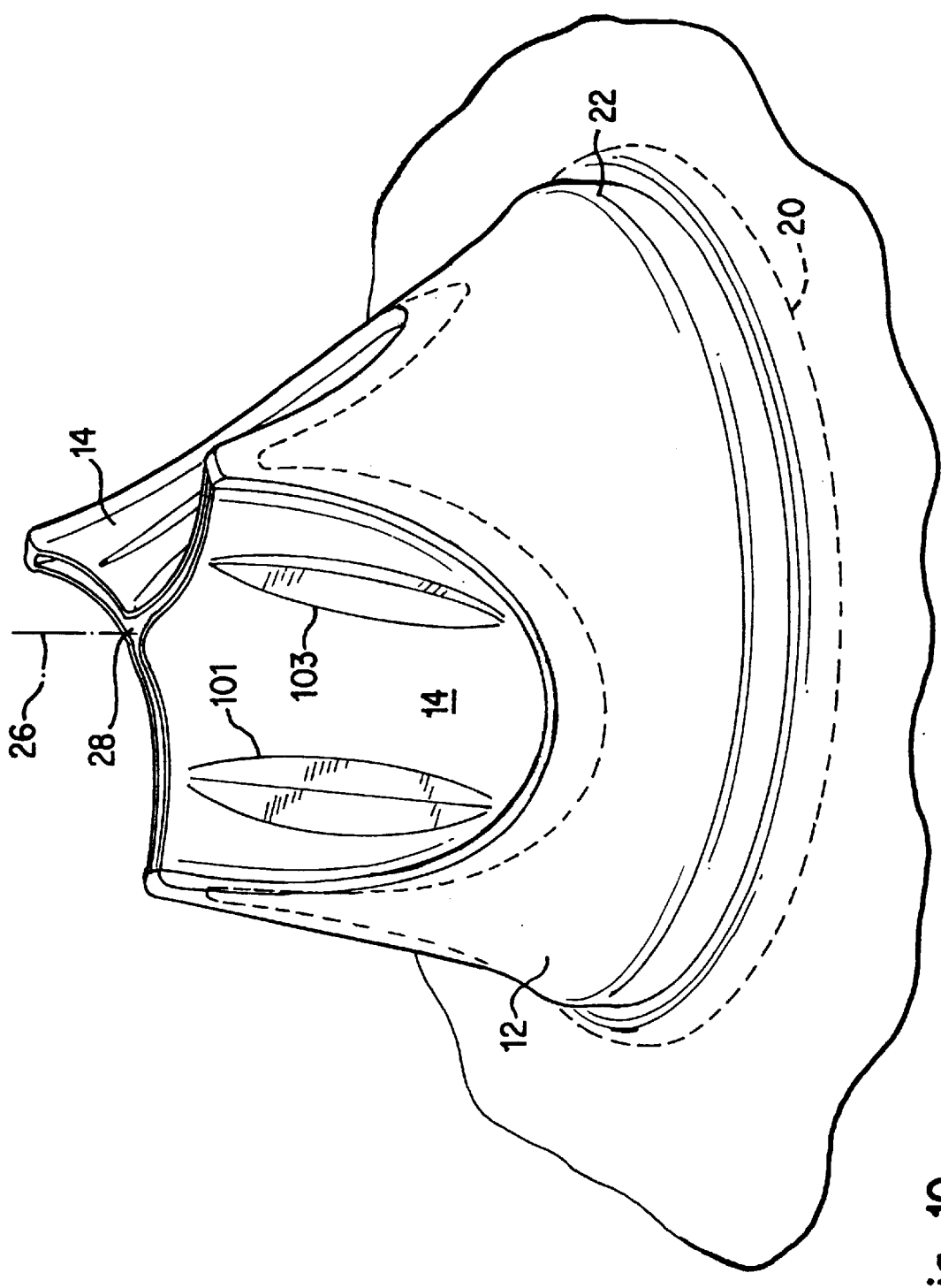
FIG. 10 is a perspective view illustrating an embodiment with two spines.
Figure 11:
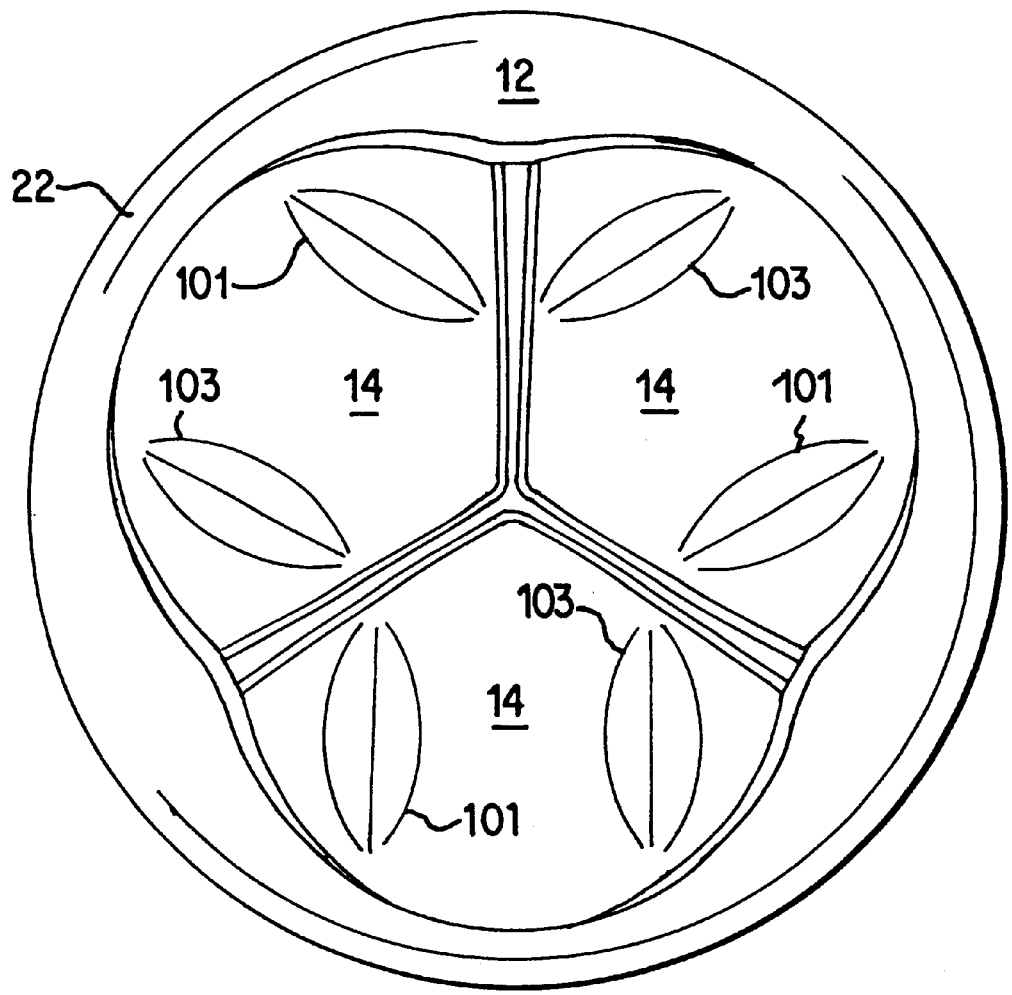
FIG. 11 is a top view of the embodiment in FIG. 10.
Figure 12:
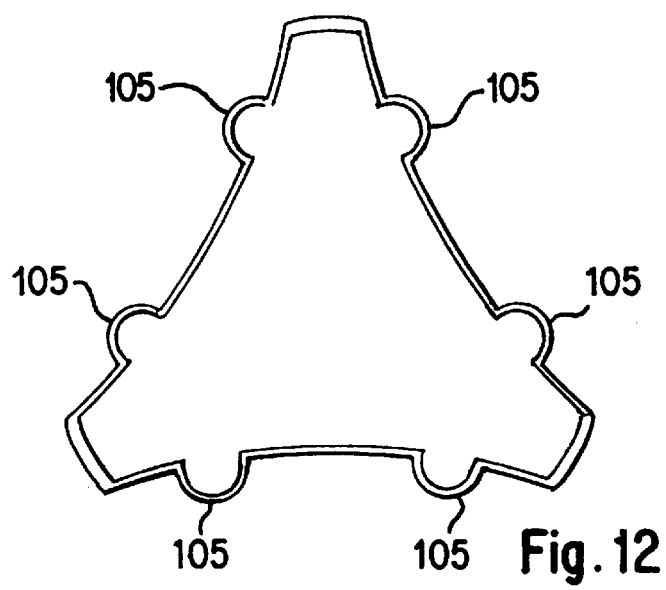
FIG. 12 is a cross sectional view of a heart valve showing one configuration of spines.
Figure 13:
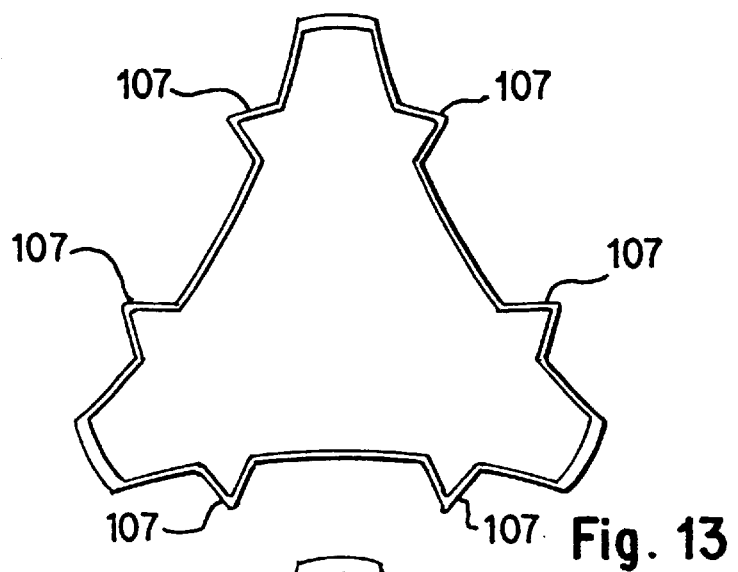
FIG. 13 is a cross sectional view of a heart valve showing another configuration of spines.
Figure 14:
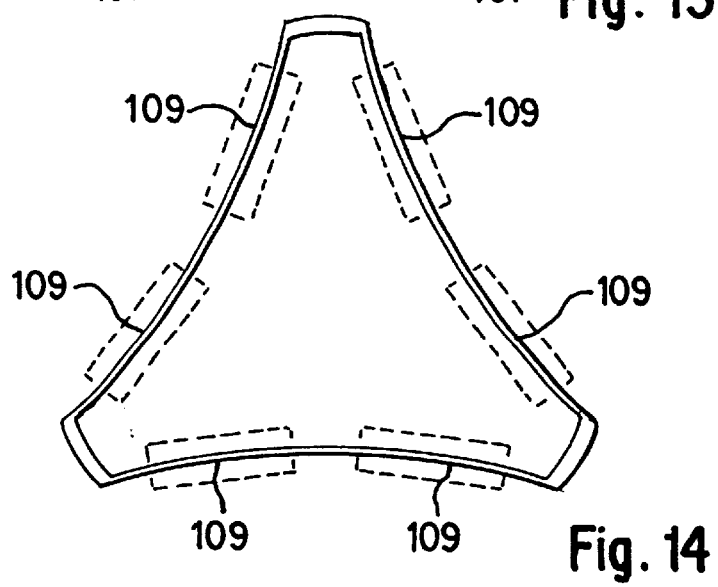
FIG. 14 is a cross sectional view of a heart valve showing another type of feature on the leaflets.

The apparatus is not limited to one feature per leaflet. Instead, more than one feature (e.g., a planar portion and a sine wave portion or weakened legs and a planar portion) can be incorporated into a single leaflet. In a preferred embodiment, an apparatus has a plurality of leaflets, one or more of the leaflets having at least two features (i.e., two or more). It has been discovered that an apparatus having a leaflet with at least two features provides surprisingly superior results compared to an apparatus with a leaflet having only one feature. As but one non-limiting example, FIGS. 10 and 11 are a perspective view and a top view, respectively, of one embodiment of a valve that includes two features on a single leaflet. The embodiment shown includes a valve body 12 and three leaflets 14, each leaflet having two features 101, 103 positioned in a generally from the base of the valve body 12 to the triple point 28. The two features 101, 103 in combination with the valve body and each leaflet 14 form a four bar mechanism which further reduces the resistance of the leaflet to buckling and facilitates opening of the valve under reduced pressure. The two features behave as hinges and divide the leaflet into three regions, i.e., the two hinges and the rest of the leaflet. Together with the valve body acting as a fixed link, these components act as a four bar mechanism which is inherently unstable to a load. By comparison, it is noted that an apparatus having a leaflet with a single feature will generally not have these physical properties. In that particular embodiment of FIG. 10, the features 101, 103 extend from the attachment edge of the leaflet to the free margin or at least proximate to the free margin to facilitate opening of the free margin on initial blood flow. This position of the features enables the free margin to open under the initial blood flow due to the hinge mechanism and the vulnerability of the four bar mechanism. Similar to the embodiments shown in FIGS. 1–8 and described with reference thereto, the features may take on various forms, shapes and geometries. By way of example, FIGS. 12 and 13 illustrate two geometries 105 and 107 of the features. FIG. 14 illustrates flat or thinned portions of the leaflets which form features susceptible to the opening flow of the blood. The flat or thinned portions are shown at 109 in the boxed area of the leaflet cross section. The features, whether planed areas or thinned areas, break the continuity of the leaflet and facilitate opening of the leaflet.

Figure 9:
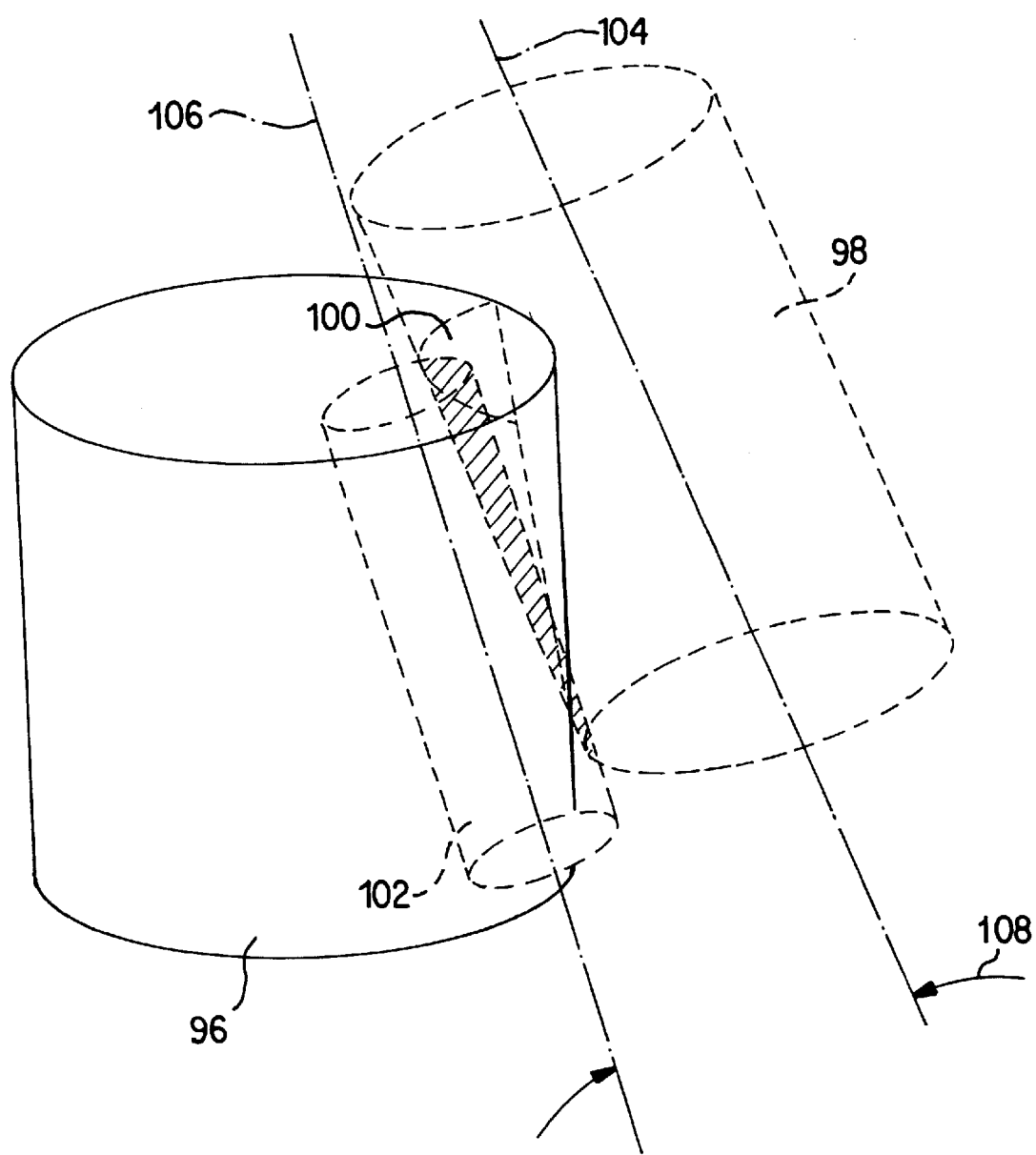
FIG. 9 is a perspective view of the geometry of a leaflet according to the present invention.

For ease of manufacture, the shape of the valve leaflets is preferably determined by the intersection of solid cylinders, as illustrated in FIG. 9. A cylinder 96 represents the shape of the valve body. The intersection of the valve body cylinder 96 with a second cylinder 98 creates the shape of a cylindrical leaflet 100. A cylindrical feature is added to the shape of the leaflet by intersecting a third cylinder 102 with the intersection of the first two. The second cylinder 98 and the third cylinder 102 each have longitudinal axes 104 and 106, respectively. Preferably, the point of closest approach of the two axes 104 and 106 is above the intersection of the leaflet and the valve body (where the triple point is considered to be above the bottom point). Preferably, the two axes 104 and 106 intersect above the intersection of the leaflet and the valve body. Preferably, the two axes 104 and 106 are not parallel. Even more preferably, the angle 108 between the two axes is greater than one degree. Even more preferably, the angle 108 between the two axes is about three degrees.

The features shown in the embodiments above can also be positioned on the leaflets in an inclined orientation or a generally vertical orientation as described in reference to other embodiments above.

Further, each leaflet may have a different combination of features or one or more of the leaflets on a valve may be entirely free of features. Each feature may incorporate a variety of mechanisms to increase the leaflet's susceptibility to buckling, including incorporating one or more of the feature shapes within a single feature and varying the material thickness within the feature. Moreover, the features described above may be added to valves other than tri-leaflet heart valves, including single leaflet heart valves, bi-leaflet heart valves or valves having more than three leaflets.

The foregoing describes preferred embodiments of the invention and is given by way of example only. The invention is not limited to any of the specific features described herein, but includes all variations thereof within the scope of the appended claims.

What is claimed is:

1. A heart valve comprising
   a valve body; and
   a plurality of flexible leaflets coupled to the valve body, wherein each of the leaflets has an open position and a closed position, wherein at least one of the leaflets comprises at least two buckle features, wherein each buckle feature is independently selected from the group consisting of a spine, a planar region, a semicircular region, a folded region, a peaked region, a ridged region, a region that is thinner than the rest of the leaflet, end a sine-wave shaped region.

2. The heart valve of claim 1, wherein at least one of the leaflets comprises only two buckle features.

3. The heart valve of claim 1, wherein the buckle features are formed as part of the leaflets.

4. The heart valve of claim 1, wherein the buckle features each comprise (a) a spine or (b) a region that is thinner than the rest of the leaflet.

5. The heart valve of claim 1, wherein each of the leaflets has a line that extends from a bottom point of the leaflet to the center of the free margin, wherein the buckle features are symmetrically disposed around the line.

6. The heart valve of claim 1, wherein each of the leaflets has a line that extends from a bottom point of the leaflet to the center of the free margin, wherein the buckle features are asymmetrically disposed around the line.

7. The heart valve of claim 1, wherein each of the leaflets has a line that extends from a bottom point of the leaflet to the center of the free margin, wherein the buckle features have that are parallel or oblique to the line.

8. A heart valve comprising
   a valve body; and
   a plurality of flexible leaflets coupled to the valve body, the plurality of leaflets having an open position and a closed position, each of the plurality of leaflets comprising a belly when the plurality of leaflets are in their respective closed positions, the belly of at least one of the plurality of leaflets having a continuous curvature except for two non-continuous portions.

9. The heart valve of claim 8, wherein at least one of the non-continuous portions is generally cylindrical.

10. The heart valve of claim 8, wherein at least one of the non-continuous portions is generally planar.

11. The heart valve of claim 8, wherein the non-continuous portions have longitudinal axes and cross-sections of the non-continuous portions generally perpendicular to the longitudinal axes of the non-continuous portions are V-shaped.

12. A heart valve comprising
    a valve body; and
    a plurality of flexible leaflets coupled to the valve body, each leaflet having a thickness, at least one of the plurality of leaflets comprising at least two buckle-susceptible portions, the thickness of the buckle-susceptible portions being different from the thickness of the remaining portion of the leaflet.

13. The heart valve of claim 12, wherein the thickness of the buckle-susceptible portions is less than the thickness of the remaining portion of the leaflet.

14. The heart valve of claim 12, wherein the thickness of the buckle-susceptible portion is not uniform.

15. The heart valve of claim 8, wherein each belly is symmetrical about a belly axis, the non-continuous portions having longitudinal axes, the belly axis not coinciding with the axes of the non-continuous portions.

16. The heart valve of claim 8, wherein each leaflet has a center of a free margin and a bottom point, the non-continous portions having longitudinal axes extending along a line from the bottom point of the leaflet to the center of the free margin of the leaflet.

17. A heart valve comprising,
    a valve body; and
    a plurality of flexible leaflets coupled to the valve body, each leaflet having an open position and a closed position,
    wherein at least one of the plurality of leaflets comprises at least two expansion features, the expansion features configured so that the leaflet has more surface area in the open position than it has in the closed position.

\* \* \* \* \*

UNITED STATES PATENT AND TRADEMARK OFFICE
CERTIFICATE OF CORRECTION

PATENT NO.     : 6,666,885 B2
DATED          : December 23, 2003
INVENTOR(S)    : Riyad Moe It is certified that error appears in the above-identified patent and that said Letters Patent is hereby corrected as shown below:

Column 7,
Line 42, "end" should be -- and --.

Column 8,
Line 4, after "have" insert -- axes --.
Lines 42-43, "non-continous" should be -- non-continuous --.

Signed and Sealed this

Fourth Day of May, 2004

JON W. DUDAS
*Acting Director of the United States Patent and Trademark Office*